United States Patent [19]

Schumacher et al.

[11] Patent Number: 5,385,881
[45] Date of Patent: Jan. 31, 1995

[54] HERBICIDAL AGENTS

[75] Inventors: Hans Schumacher, Flörsheim am Main; Hans P. Huff, Eppstein/Taunus; Erwin Hacker, Hochheim am Main, all of Germany

[73] Assignee: Hoechst Aktiengesellschaft, ·Frankfurt am Main, Germany

[21] Appl. No.: 531,926

[22] Filed: Jun. 1, 1990

[30] Foreign Application Priority Data

Jun. 5, 1989 [DE] Germany .............................. 3918288

[51] Int. Cl.$^6$ .............................................. A01N 43/54
[52] U.S. Cl. ...................................... 504/136; 504/141
[58] Field of Search ........................... 71/92, 126, 127; 504/136, 141

[56] References Cited

U.S. PATENT DOCUMENTS 4,601,747  7/1986  Willms et al. ............................ 71/92

OTHER PUBLICATIONS

Zschaler; Chem Abstract, "Effect of Liquid Quantity, Application Method . . . " vol. 96, 1982, 137877t.
Paul; Chem Abstract, "A New Broad Spectrum Cereal Herbicide Based on Flulokypyr," vol. 104, 1986, 124906k.

Primary Examiner—Glennon H. Hollrah
Assistant Examiner—Brian M. Burn
Attorney, Agent, or Firm—Curtis Morris & Safford

[57] ABSTRACT

Combinations comprising 3-(4,6-dimethoxy-2-pyrimidinyl)-1-[(N-methyl-N-methylsulfonyl)aminosulfonyl]-urea (I) and ioxynil (II) and/or bromoxynil (III) are useful herbicides with synergistic properties.

12 Claims, No Drawings

HERBICIDAL AGENTS

The invention relates to herbicidal agents which contain the compound 3-(4,6-dimethoxy-2-pyrimidinyl)-1-[(N-methyl-N-methylsulfonyl)aminosulfonyl]-urea of the formula

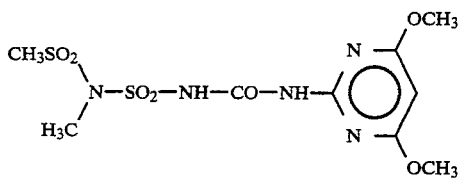

in combination with ioxynil (3,5-diiodo-4-hydroxybenzonitrile; II) and/or bromoxynil (3,5-dibromo-4-hydroxybenzonitrile; III).

The active compound I is known from EP-A 131,258 (U.S. Pat. No. 4,601,747). Ioxynil and bromoxynil have been used for a long time as herbicidal commercial products and are described in detail, for example, in "Pesticide Manual", 7th edition 1983 or 8th edition 1987, The British Crop Protection Council, London.

The compounds of the formula II and III are employed in the form of their commercially available derivatives, for example as octanoates or as Na and K salts. Surprisingly, when the combinations according to the invention are used, they show a super-additive (synergistic) effect which was not to be expected on the basis of the action of the individual components.

The mixing ratios of components I and II and/or III can vary within wide limits without the synergistic action being lost. The mixing ratios can vary, for example, between 1:1 and 1:100, preferably between 1:2 and 1:60.

The application amounts of the active compound mixtures according to the invention are as a rule between 0.07 and 1.0 kg/ha, preferably 0.1 to 1 kg/ha. For application outdoors, the application amount is preferably between 0.2 and 1 kg/ha.

As regards compound I, the application amount is preferably between 5 g/ha and 50 g/ha. 50 to 500 g/ha of the compounds II and III are preferably employed.

The combinations according to the invention can be used for controlling numerous annual and perennial weeds, such as, for example, Galium aparine (cleavers), Stellaria media (common chickweed), Matricaria sp. (mayweed), Sinapis sp. (charlock) and others. Because they are not harmful to crop plants, they can be used for the selective control of weeds in numerous crops of useful plants, in particular in rice, wheat, barley and oats.

The agents according to the invention can be marketed in the customary formulations familiar to the expert, for example as wettable powders, dusting agents, granules, dispersion concentrates, emulsifiable concentrates or solutions for spraying. The formulated agents in this case in general contain the active compounds in concentrations of 2 to 95% by weight.

These individual types of formulation are known in principle and are described, for example, in: Winnacker-Küchler, "Chemische Technologie (Chemical Technology)", Volume 7, C. Hauser Verlag Munich, 4th edition 1986; van Falkenberg, "Pesticides Formulations", Marcel Dekker N.Y., 2nd edition 1972–73; and K. Martens, "Spray Drying Handbook", 3rd edition 1979, G. Goodwin Ltd. London.

The necessary formulation auxiliaries, such as inert materials, surfactants, solvents and further additives, are likewise known and are described, for example, in: Watkins, "Handbook of Insecticide Dust Diluents and Carriers", 2nd edition, Darland Books, Caldwell N.J.; H. V. Olphen, "Introduction to Clay Colloid Chemistry", 2nd edition, J. Wiley & Sons, N.Y.; Marschen, "Solvents Guide", 2nd edition, Interscience, N.Y. 1950; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxid-addukte (Surface-active Ethylene Oxide Adducts)", Wiss. Verlagsgesell., Stuttgart 1976; Winnacker-Küchler, "Chemische Technologie (Chemical Technology)", Volume 7, C. Hauser Verlag Munich, 4th edition 1986.

On the basis of these formulations, combinations with other pesticidally active substances, fertilizers and/or growth regulators can also be prepared, for example in the form of a finished formulation or as a tank mix.

Wettable powders are preparations which are uniformly dispersible in water and which, in addition to the active compound and apart from a diluent or inert substance, also contain wetting agents, for example polyoxyethylated alkylphenols, polyoxyethylated fatty alcohols or polyoxyethylated fatty amines, alkanesulfonates or alkylbenzenesulfonates, and dispersing agents, for example sodium ligninsulfonate, sodium 2,2'-dinaphthylmethane-6,6'-disulfonate, sodium dinaphthylmethanedisulfonate, sodium dibutylnaphthylsulfonate or sodium oleyl methyl taurate.

Emulsifiable concentrates are prepared by dissolving the active compound in an organic solvent, for example butanol, cyclohexanone, dimethylformamide, xylene or higher-boiling aromatics or hydrocarbons, one or more emulsifiers being added. Examples of emulsifiers which can be used are: calcium alkylarylsulfonates, such as Ca dodecylbenzenesulfonate, or nonionic emulsifiers, such as fatty acid polyglycol esters, alkylaryl polyglycol ethers, such as polyoxyethylated alkylphenols, fatty alcohol polyglycol ethers, propylene oxide-ethylene oxide condensation products, alkyl polyethers, polyethoxylated fatty amines, such as polyethoxylated oleyl- or stearylamine, sorbitan fatty acid esters, polyoxyethylene sorbitan fatty acid esters or polyoxyethylene sorbitol esters.

Dusting agents are obtained by grinding the active compound with finely divided solid substances, for example talc or naturally occurring clays, such as kaolin, bentonite, pyrophillite or diatomaceous earth. Soil or scattering granules can be prepared either by spraying the active compound onto adsorbent granular inert material or by application of active compound concentrates to the surface of carrier substances, such as sand or kaolinites, or of granular inert material by means of adhesives, for example polyvinyl alcohol, sodium polyacrylate or mineral oils. Suitable active compounds can also be granulated in the manner customary for the preparation of fertilizer granules—if desired as a mixture with fertilizers.

The total active compound concentration in wettable powders varies between about 10% and 95%, the remainder comprising the abovementioned formulation additives. In emulsifiable concentrates, the active compound concentration is about 10% to 80%. Dust-like formulations usually contain 5% to 20% of active compounds, and solutions for spraying about 2% to 20%. In granules, the active compound content partly depends on the form (liquid or solid) in which the active compounds are present and which granulation auxiliaries, fillers and the like are used.

The content in water-dispersible granules is in general between 10 and 90% by weight.

In addition, the active compound formulations mentioned contain, if appropriate, the particular customary adhesives, wetting agents, dispersing agents, emulsifiers, penetration agents, solvents, fillers or carrier substances.

For use, the formulations in their commercially available form are diluted, if appropriate, in the customary manner, for example by means of water in the case of wettable powders, emulsifiable concentrates, dispersions and water-dispersible granules. Dust formulations, soil and scattering granules and solutions for spraying are usually not diluted further with additional inert substances before use.

The combinations according to the invention of the active compounds I and II (III) can be used by the pre-emergence or post-emergence process. In this process, the active compounds I and II or III are applied individually in succession or together to the plants or their cultivation area. Use by the post-emergence process is preferred.

The application amount required for the compounds of the formula (I) varies according to the external conditions, such as temperature, humidity, type of herbicide used and the like.

Mixtures or mixed formulations with other active compounds, such as, for example, insecticides, acaricides, herbicides, fertilizers, growth regulators or fungicides, are also possible if appropriate.

The following examples serve to illustrate the invention:

A. FORMULATION EXAMPLES a) A dusting agent is obtained by mixing 10 parts by weight of active compound mixture and 90 parts by weight of talc, as an inert substance, and comminuting the mixture in a hammer mill.

b) A wettable powder which is readily dispersible in water is obtained by mixing 25 parts by weight of active compound mixture, 64 parts by weight of kaolin-containing quartz, as an inert substance, 10 parts by weight of potassium ligninsulfonate and 1 part by weight of sodium oleoyl methyl taurate, as a wetting and dispersing agent, and grinding the mixture in a pinned disk mill.

c) A dispersion concentrate which is readily dispersible in water is obtained by mixing 20 parts by weight of active compound mixture with 6 parts by weight of alkylphenol polyglycol ether (®Triton X 207), 3 parts by weight of isotridecanol polyglycol ether (8 ethylene oxide) and 71 parts by weight of paraffinic mineral oil (boiling range, for example, about 255° to 377° C.), and grinding the mixture to a fineness of less than 5 microns in a bead mill.

d) An emulsifiable concentrate is obtained from 15 parts by weight of active compound mixture, 75 parts by weight of cyclohexanone, as a solvent, and 10 parts by weight of oxyethylated nonylphenol (10 ethylene oxide), as an emulsifier.

e) Water-dispersible granules are obtained by mixing
75 parts by weight of active compound mixture,
10 parts by weight of calcium ligninsulfonate,
5 parts by weight of sodium lauryl sulfate,
3 parts by weight of polyvinyl alcohol and
7 parts by weight of kaolin grinding the mixture in a pinned disk mill and granulating the powder in a fluidized bed by spraying on water as the granulating liquid.

f) Water-dispersible granules are also obtained by homogenizing and precomminuting
25 parts by weight of active compound mixture,
5 parts by weight of sodium 2,2'-dinaphthylmethane-6,6'-disulfonate,
2 parts by weight of sodium oleoyl methyl taurate,
1 parts by weight of polyvinyl alcohol,
17 parts by weight of calcium carbonate and
50 parts by weight of water
on a colloid mill, subsequently grinding the mixture on a bead mill, atomizing the resulting suspension in a spraying tower by means of a one-component nozzle and drying the product.

g) Extruded granules are obtained by mixing 20 parts by weight of active compound mixture, 3 parts by weight of sodium ligninsulfonate, 1 part by weight of carboxymethylcellulose and 76 parts by weight of kaolin and grinding the mixture and moistening it with water. This mixture is extruded and then dried in a stream of air.

B. BIOLOGICAL EXAMPLES

The following experiments were carried out under greenhouse conditions.

In all cases, a distinction was made between the calculated effectiveness and the observed effectiveness of the combinations.

The calculated effectiveness theoretically to be expected of a combination is determined in accordance with the formula of S. R. Colby: Calculation of synergistic and antagonistic responses of herbicide combinations, Weeds 15, (1967), 20–22.

This formula states $$E = X + Y - \frac{X \times Y}{100}$$

in which $X = \%$ damage by herbicide A at an application amount of X kg/ha;

$Y = \%$ damage by herbicide B at an application amount of Y kg/ha;

E = the damage to be expected by the herbicides A+B at an application amount of X+Y kg/ha.

If the actual damage is greater than that to be expected mathematically, the action of the combination is more than additive, i.e. a synergistic action effect exists.

EXPERIMENTAL PROCEDURE

The test plants were grown in pots in a greenhouse.

The active compounds were in each case applied by themselves or in combinations (tank mixes) in the stated dosages when the wheat (*Triticum aestivum*), the barley (*Hordeum vulgare*) and the oats (*Avena sativa*) had reached the 4–5 leaf stage and *Galium aparine*, *Stellaria media* and *Matricaria chamomilla* had reached a growth height of 5–10 cm. 3 weeks after the application, the herbicidal action was evaluated by rating the plants. The data relate to percentage values of the damage. The results are shown in the following table, the values in parentheses corresponding to the expected values calculated from the Colby formula.

TABLE 1

| Active compound | Dose g of active substance/ ha | Damage in % on | | | | | |
|---|---|---|---|---|---|---|---|
| | | Galium aparine | Stellaria media | Matricaria chamonilla | Triticum aestivum | Hordeum vulgare | Avena sativa |
| I | 5 | 26 | 20 | 10 | 0 | 0 | 0 |
| | 7.5 | 35 | 27 | 18 | 0 | 0 | 0 |
| | 10 | 40 | 35 | 25 | 0 | 0 | 0 |
| | 15 | 48 | 43 | 35 | 0 | 0 | 0 |
| | 25 | 60 | 55 | 50 | 0 | 0 | 0 |
| II | 50 | 25 | 30 | 30 | 0 | 0 | 0 |
| | 75 | 33 | 40 | 38 | 0 | 0 | 0 |
| | 150 | 40 | 55 | 45 | 0 | 0 | 0 |
| | 300 | 65 | 70 | 70 | 0 | 0 | 0 |
| III | 50 | 30 | 10 | 35 | 0 | 0 | 0 |
| | 75 | 37 | 15 | 40 | 0 | 0 | 0 |
| | 150 | 45 | 30 | 50 | 0 | 0 | 0 |
| | 300 | 68 | 45 | 75 | 0 | 0 | 0 |
| I + II | 25 + 50 | 88 (70) | 90 (69) | 82 (65) | 0 | 0 | 0 |
| | 15 + 75 | 84 (69) | 86 (66) | 76 (60) | 0 | 0 | 0 |
| | 7.5 + 150 | 79 (61) | 87 (53) | 70 (55) | 0 | 0 | 0 |
| | 7.5 + 300 | 100 (78) | 100 (79) | 95 (76) | 0 | 0 | 0 |
| | 5 + 300 | 95 (75) | 93 (76) | 90 (73) | 0 | 0 | 0 |
| I + III | 25 + 50 | 92 (72) | 69 (60) | 89 (68) | 0 | 0 | 0 |
| | 15 + 75 | 89 (68) | 63 (52) | 80 (61) | 0 | 0 | 0 |
| | 7.5 + 150 | 83 (65) | 59 (49) | 77 (59) | 0 | 0 | 0 |
| | 7.5 + 300 | 100 (80) | 78 (60) | 100 (80) | 0 | 0 | 0 |
| | 5 + 300 | 98 (77) | 70 (54) | 88 (78) | 0 | 0 | 0 |

We claim:

1. A herbicidal composition which contains a synergistic mixture of 3-(4,6-dimethoxy-2-pyrimidinyl)-1-[N-methyl-N-methylsulfonyl)aminosulfonyl]-urea of the formula

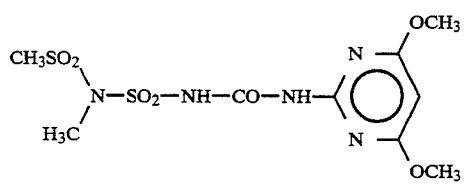

in combination with ioxynil (II) or bromoxynil (III) in a weight ratio of 1:2 to 1:60 of the compounds I:II or I:III.

2. A herbicidal composition as claimed in claim 1, which contains 2–95% by weight of active compound mixture and 98–5% by weight of customary formulation auxiliaries for formulations from the group comprising wettable powders, dusting agents, granules and solutions for spraying.

3. A method of selectively or non-selectively controlling weeds, which comprises applying an effective amount of a synergistic mixture comprising the compound of the formula I in combination with compounds of the formula II or III to the plants to be treated or to their cultivation areas.

4. The method as claimed in claim 3, wherein the synergistic mixture contains the active compounds I and II (III) in a weight ratio of 1:2 to 1:60.

5. The method as claimed in claim 3, wherein the synergistic mixture is applied in an application amount of 0.07 to 1.0 kg/ha.

6. The method as claimed in claim 4, wherein the synergistic mixture is applied in an application amount of 0.07 to 1.0 kg/ha.

7. The method as claimed in claim 3, wherein the application amount is 0.1 to 1 kg/ha.

8. The method as claimed in claim 4, wherein the application amount is 0.1 to 1 kg/ha.

9. A herbicidal composition which contains as active ingredient a synergistic mixture of 3-(4,6-dimethoxy-2-pyrimidinyl)-1-[(N-methyl-N-methylsulfonyl)-aminosulfonyl]-urea of formula (I)

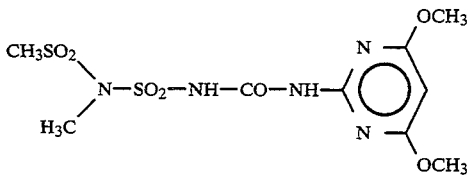

and ioxynil (II) in a weight ratio of (I):(II) of from 1:1 to 1:60.

10. A herbicidal composition which contains as active ingredient a synergistic mixture of 3-(4,6-dimethoxy-2-pyrimidinyl)-1-[N-methyl-N-methylsulfonyl-aminosulfonyl]-urea of formula (I)

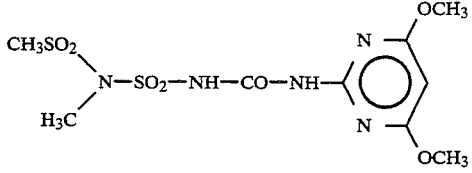

and bromoxynil (III) in a weight ratio of (I):(III) of from 1:2 to 1:60.

11. A method for selectively controlling weeds in crops of useful plants, which comprises applying an effective amount of from 0.07 to 1.0 kg/ha of a synergistic mixture as defined in claim 9 to the plants or to their cultivation area.

12. A method for selectively controlling weeds in crops of useful plants, which comprise applying an effective amount of from 0.07 to 1.0 kg/ha of synergistic mixture as defined in claim 10 to the plants or to their cultivation area.

* * * * *